United States Patent
Bauman et al.

(10) Patent No.: US 8,702,579 B2
(45) Date of Patent: Apr. 22, 2014

(54) CONTROL SYSTEM AND METHOD FOR PRECISELY GUIDING A PERCUTANEOUS NEEDLE TOWARD THE PROSTATE

(75) Inventors: Michael Bauman, Grenoble (FR); Nikolai Hungr, Grenoble (FR); Antoine Leroy, Meylan (FR); Jocelyne Troccaz, Eybens (FR); Vincent Daanen, Saint Joseph de Riviere (FR)

(73) Assignees: Koelis, Grenoble (FR); Universite Joseph Fournier, Grenoble Cedex (FR)

( * ) Notice: Subject to any disclaimer, the term of this patent is extended or adjusted under 35 U.S.C. 154(b) by 0 days.

(21) Appl. No.: 13/393,311

(22) PCT Filed: Aug. 27, 2010

(86) PCT No.: PCT/FR2010/000587
§ 371 (c)(1),
(2), (4) Date: Jun. 11, 2012

(87) PCT Pub. No.: WO2011/023866
PCT Pub. Date: Mar. 3, 2011

(65) Prior Publication Data
US 2012/0245455 A1    Sep. 27, 2012

(30) Foreign Application Priority Data
Aug. 31, 2009   (FR) ...................................... 09 04124

(51) Int. Cl.
*A61N 5/00*   (2006.01)
(52) U.S. Cl.
USPC ............ 600/1; 600/3; 600/7; 600/8; 600/424; 600/437; 600/439; 600/441

(58) Field of Classification Search
None
See application file for complete search history.

(56) References Cited

U.S. PATENT DOCUMENTS

| | | | |
|---|---|---|---|
| 6,423,009 B1 | 7/2002 | Downey et al. | |
| 6,846,282 B1 | 1/2005 | Ford | |
| 6,869,390 B2 * | 3/2005 | Elliott et al. | 600/1 |
| 2003/0018232 A1 | 1/2003 | Elliott et al. | |
| 2003/0065260 A1 * | 4/2003 | Cheng et al. | 600/427 |
| 2007/0016067 A1 | 1/2007 | Webster, III et al. | |
| 2007/0270687 A1 | 11/2007 | Gardi et al. | |

FOREIGN PATENT DOCUMENTS

| | | |
|---|---|---|
| CA | 2654344 A1 | 12/2007 |
| EP | 1088524 A1 | 4/2001 |
| WO | 9831273 A1 | 7/1998 |
| WO | 9960921 A1 | 12/1999 |
| WO | 2007085953 A1 | 8/2007 |
| WO | 2009071766 A1 | 6/2009 |

* cited by examiner

*Primary Examiner* — Joel Lamprecht
(74) *Attorney, Agent, or Firm* — Bachman & LaPointe, P.C.

(57) ABSTRACT

A needle holder device for treating the prostate, involving a series of steps of inserting a needle into the prostate, has a rectal probe for ultrasonic 3D imaging and a computer for processing the image acquired by the probe and for computing the position of the needle relative to the prostate. The computer is controlled so as to periodically output information on the movement of the prostate after each of the insertion steps in order to validate the insertion parameters relative to a treatment schedule and, if need be, modifying the insertion parameters relative to the schedule in the event the movement is greater than a threshold value.

12 Claims, 6 Drawing Sheets

CONTROL SYSTEM AND METHOD FOR PRECISELY GUIDING A PERCUTANEOUS NEEDLE TOWARD THE PROSTATE

FIELD OF THE INVENTION

This invention relates to the field of devices for treating and diagnosing prostate diseases.

These devices are intended to control the displacement of a needle and the insertion thereof into the prostate in a determined direction and at a determined depth.

The treatment of prostate cancer is intended to cure the patient by destroying diseased tissue while preserving the healthy surrounding tissue. It is therefore important to be able to deliver therapeutic agents in a precise manner to cancer tissue. If the agent is placed with inadequate precision, it may act on healthy tissue, and potentially on functional structures such as the bladder, the rectum or the urethra. In these cases, the patient may suffer from conditions such as impotence or incontinence. The high rate of adverse effects for minimally invasive prostate cancer treatments can be explained by the fact that the current treatments suffer from a double failure: 1) The tools for delivering therapeutic agents (for example, a puncture needle containing a radioactive seed in brachytherapy) can be placed at a distance from the target due to factors such as mobility of the prostate or bending of the needle, and 2) these distances are not detected prior to delivery of the agent.

For certain treatments, a very precise delivery of the therapeutic agents makes it possible to cover all of the tissue to be treated regularly and with a sufficient cumulative effect or dose (brachytherapy, cryotherapy, HIFU, for example). The risk of recurrence, associated with the under-treatment of cancerous areas, is therefore highly dependent on the precision of implementation of the treatment.

In fact, until now, prostate treatments have been conducted in a general manner, on the entire gland. The main reasons are the uncertainty of the localization of cancer tissue with the current diagnostic means and the multifocal nature of prostate cancer. The third reason is the lack of precision of the current treatment devices, as the risk of missing or under-dosing a localized target is relatively high.

The diagnosis of prostate cancer is affected by the same problem of imprecision due to the imprecision of the devices and the lack of management of the soft and mobile environment of the prostate. Better precision is necessary in order to be capable of providing a more reliable and complete diagnosis, in particular with information on the localization of cancerous areas, which may also be used to plan and guide focused treatments.

In conclusion, there is therefore a serious need to be capable of guiding diagnostic tools and therapeutic agents with maximum precision to the origin of the cancer, in order to improve the reliability of the diagnosis, and to minimize the adverse effects, recurrences and morbidity associated with the treatment. It is also desirable to improve the detection of situations in which the device for delivering the agent has not reached the target before the agent is delivered.

PRIOR ART

In this context of precise diagnosis and treatment of prostate cancer, the prior art has proposed various solutions making it possible to improve the traceability on the organ of needle penetration areas, as well as the localization of cancerous areas.

A first solution, described in international patent WO 2009 071766 relates to a prostate imaging method comprising steps of recording and processing images acquired by the ultrasonic head of a rectal probe equipped with an active puncture guide. This method comprises steps of processing at least some of the images acquired by the probe in order to calculate transformations toward a reference image system with the initial position of the prostate, at least some of the images acquired during successive punctures including the localization of the different positions of the needle, which are recorded in order to show their representations in a single image including at least some of the prostate. This prior art patent also relates to a prostate imaging system implementing said prostate imaging method.

This solution improves the acquisition of graphic information on the prostate, and enables the matching of different images of the prostate, acquired with complementary imaging systems, as well as by a rectal probe integrated with the treatment needle. It therefore enables the guiding and localizing of the needle with respect to areas of interest in the prostate to be improved.

This imaging system can be used for both devices manually held by a surgeon and automated devices.

The prior art also includes control methods, sometimes associated with automated devices for performing biopsies and prostate treatments.

The closest prior art is described in the American patent US 2007 0270687, which describes a registration method for obtaining updates between 3D ultrasound images in order to monitor the movement of an instrument in the image reference system by using the differences between the two images by subtraction. One application proposed in this prior art document is monitoring of the movement of the end of a brachytherapy needle in order to enable adaptive dosimetry and to overcome needle-positioning errors.

Another prior art document close to the present invention is the Canadian patent CA 2654344, which describes a device and a method for the positioning and the insertion of a needle around a fixed point (remote center of motion). According to an application described in this document, this device and technique can be used to position a biopsy needle, by visually comparing 3D ultrasound images in order to check the movement or swelling of the prostate after the needle is removed.

Yet another prior art document close to the present invention is the American patent U.S. Pat. No. 6,423,009, which describes a system for guiding percutaneous tools for prostate therapy using 3D ultrasound images. An example of use the use of the technique involves the positioning of cryotherapy probes in prostate cryotherapy. In this example, a method for positioning probes while checking the proper positioning of the needles with respect to the plan is described.

The international patent application WO 2007 085953 is another prior art document. It describes a device and a method for inserting a needle according to a predetermined trajectory, and at a predetermined depth, in order to reach a target area of tissue of a soft organ, with control by ultrasound imaging. The applications proposed in this prior art document are biopsy of the prostate or brachytherapy of the prostate. The method implements a conical approach area through the perineal wall. The needle passes through the patient's skin through a pivot point. The orientation of the needle support is ensured by spherical joints.

The American patent U.S. Pat. No. 684,628 B describes means for brachytherapy performed with a needle for injecting a radioactive product into an organ such as the prostate.

Markers placed on the patient's body define a system of coordinates enabling the real-time analysis of the displacement of the needle within the reference system of the patient. An alternative solution consists of using anatomical markers.

The patent EP 1088524 describes, in general, a system and a method for implementing prostate brachytherapy based on a reconstructed 3D ultrasound image, preoperative planning of the insertion of needles including segmentation of the surrounding organs and a peri-operative evaluation of the placement and deflection of the needles with respect to the plan. There is no mention of three-dimensional quantification of the movement of the prostate in this invention.

The patent US 2003 0018232 describes an automated system for implanting radioactive seeds. The principle of positioning a needle at a width, height and depth in the organ, in order to insert a radioactive seed therein, is described. The system is calibrated with respect to the organ (the prostate) by the adjustment of a basic plane with respect to the organ seen in the ultrasound. The ultrasound probe is interdependent with the robot and moved according to an axis parallel to the axis of insertion of the needles. During the insertion procedure, a plane-by-plane ultrasound acquisition of the organ can be sequenced so as to make a registration and consequently adapt the basic needle insertion plane. As in patent EP 1088524, the 3D movement of the prostate during insertion of a needle cannot be taken into account for the automatic and precise compensation of the plan with respect to the organ.

The patent US 2007 0016067, even though it describes an automated system and method for puncture under peri-operative imaging, does not take into account, in its control loop, the relative position of the puncture tool with respect to the targeted organ.

TECHNICAL PROBLEM

As described above, the known solutions are not entirely satisfactory because the prostate is a deformable and mobile organ. The prior art solutions are therefore affected by modifications of the organ and do not enable truly precise localization. This invention is based on a precise automatic quantification of the movement of the prostate obtained from a comparison between an instantaneous 3D image of the prostate after insertion of a needle and a 3D reference image. The invention takes advantage of the instantaneous 3D ultrasound, which, unlike reconstructed 3D ultrasound, instantaneously generates a dense and coherent volume, without moving the probe or the organ.

The movements of the prostate, consisting both of displacements and deformations, indeed result in different phenomena:
  Under the pressure of a puncture or treatment needle, the prostate is deformed and is displaced within the human body.
  The punctures cause lesions, inducing swelling of the prostate during the intervention. The movements of the patient, in particular respiration, also produce deformations and displacements the prostate.
  To obtain a high-quality image, the rectal probe must come into contact with the rectal wall close to the prostate and exert a light pressure also producing deformation and displacement of the prostate.

The solutions of the prior art do not take into account the movements of the prostate either automatically or during the needle insertion time. In addition, this evaluation of movements is not used in order to adapt the guiding of the needle to the prostate reference system during insertion of said needle.

SOLUTION PROVIDED BY THE INVENTION

The objective of the invention is to overcome these disadvantages by proposing a device enabling the movements of the prostate to be overcome automatically and the guiding of the needle during its insertion to be adapted, so as to improve the precision of localized samples or treatments of the prostate.

The invention also enables the distribution of the treatment dose and the protection of healthy tissue and critical surrounding structures to be improved by more precisely taking into account the configuration and position of the prostate at the time of the treatment.

To this end, the invention also relates, according to its most general interpretation, to a needle holder device for a prostate treatment involving a sequence of steps of inserting a needle into the prostate, comprising a 3D rectal ultrasound imaging probe and a computer for processing the image acquired by said probe and for calculating the position of the needle with respect to the prostate, characterized in that the computer is commanded so as to periodically deliver information on the movement of the prostate after each of said insertion steps in order to validate the insertion parameters with respect to a treatment plan, and, as the case may be, to modify the insertion parameters with respect to said plan in the event of a movement having a value greater than a threshold value.

The term "penetration step" in the present patent means:
  a step in which the needle is displaced from a position outside the organ to a position in which the active head is positioned inside the organ,
  as well as a step in which the needle is displaced between a first position, in which the active head is positioned inside the organ, and a second position inside the organ.

According to a first alternative, said modification of insertion parameters consists of modifying the plan.

According to a second alternative, said modification of insertion parameters consists of modifying the insertion parameters by a new displacement of the needle.

According to an advantageous implementation, the information relating to the movement of the prostate is calculated by comparing the instantaneous image delivered by the rectal probe with a reference image of the prostate and by calculating quantitative information on the modifications between said images.

According to an alternative, the distance between a characteristic point of the needle in the instantaneous prostate reference system and said characteristic point of the needle in the prostate reference system of the plan is calculated, with said distance then being compared to said threshold value in order to conditionally validate the insertion parameter.

According to a particular embodiment, the device according to the invention comprises a support extended by a rectal probe and comprising a needle holder, which device comprises means for determining the relative orientation of the needle holder with respect to the acquisition volume of said rectal probe.

This determination of the orientation of the needle holder with respect to the acquisition volume can be performed by mechanical construction by position sensors or by image processing.

Preferably, the needle holder is powered and controlled with respect to movement information, and comprises means for generating a signal representing each new insertion step.

According to a particular alternative, the needle holder can be oriented so as to modify the insertion axis according to said plan.

According to a particular embodiment, the device comprises a support interdependent with the rectal probe, associated with a pivotably connected needle holder assembly, consisting of two primary parallel drive tables each connected to a secondary perpendicular drive table, in which the needle holder is supported by a cross member rotatably connected with respect to said secondary drive tables, in which said cross member extends perpendicularly to the axis of displacement of said secondary tables and the axis of displacement of said primary tables.

Preferably, the needle holder of this last embodiment comprises stress-limiting means mechanically disengaging the driving of the needle support with respect to the needle holder when the resistance to insertion exceeds a threshold value corresponding to the situation of contact with the pubic bone.

According to an alternative, the device comprises a support associated, on the one hand, with a rectal probe and, on the other hand, with needle holder positioning means.

The invention can be better understood in view of the following description, concerning a non-limiting example of the embodiment of the invention, with reference to the appended drawings, in which:

FIG. 1 shows a diagrammatic view of a device according to the prior art.

Figure 1:
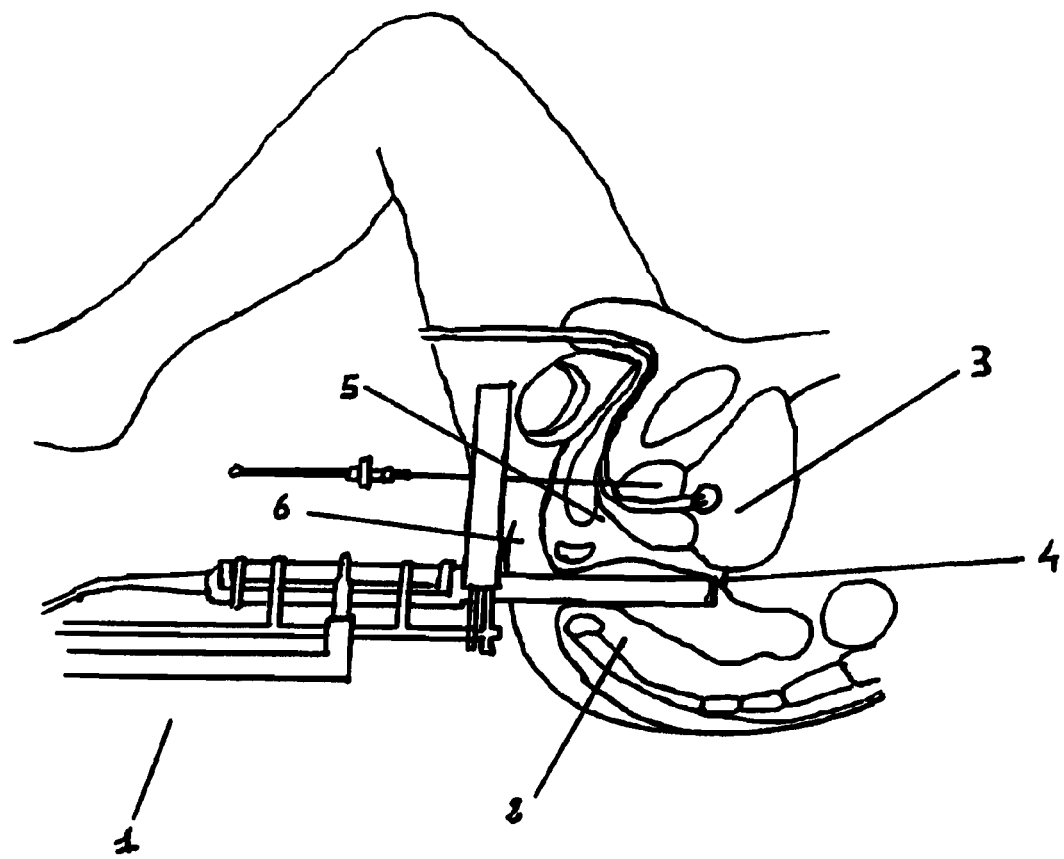
FIG. 1 shows a diagrammatic view of an device according to the prior art.

It comprises a support (1) on which a rectal probe (2) is attached, the head of which is positioned near the prostate (4) from which it is separated by the perineal wall. The head comprises ultrasound scanning imaging means enabling an image of the prostate to be produced during the intervention.

A needle (2) is handled by the surgeon, with the assistance of a guide (6) facilitating the positioning of the needle (2), which passes through the perineal wall in order to penetrate the prostate (4) according to a predefined orientation and plan.

This needle can be a hollow needle for producing a series of biopsies according to a determined plan, making it possible to detect not only the presence of a cancerous tumor, but also specifically which areas of the prostate have cancerous proliferations.

This needle can also be intended for "low-dose" prostate brachytherapy, for the treatment of the prostate gland. This treatment consists of implanting, under ultrasound monitoring of the iodine$_{125}$ seeds in the prostate.

These seeds deliver continuous irradiation for around one year. The prostate is thus treated in its entirety at a high dose, while the functional tissues located in the prostate or near the prostate (such as the bladder, rectum and urethra) receive low irradiation. The needles are implanted in the prostate, under ultrasound monitoring, transperineally (they pass directly through the skin of the perineum between the anus and the bursae). The number of needles and the number of seeds are dependent on the volume of the prostate. When the needles are properly inserted into the prostate, the radioactive seeds are inserted through the latter, after which the needles are removed.

Figure 2:
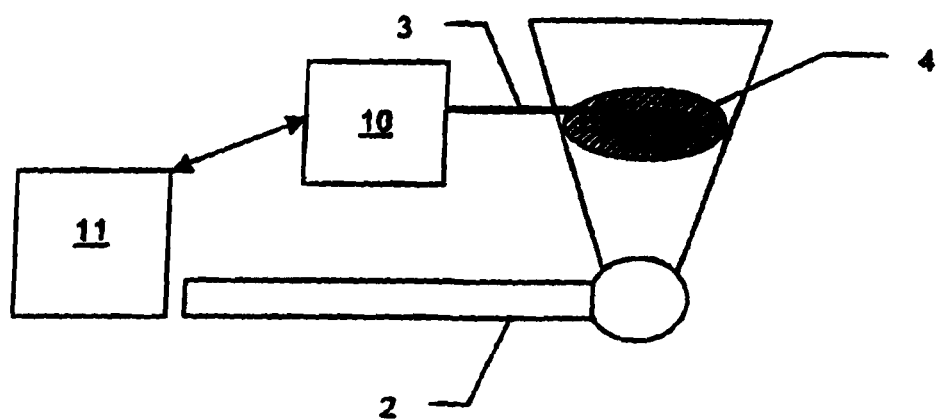
FIG. 2 shows a diagrammatic view of an device according to the invention.

FIG. 2 shows a diagrammatic view of the device according to the invention.

The displacement of the needle (3) is controlled by a powered robot (10) in the example described. The rectal probe (2) provides a 3D ultrasound image that is used by a computer (11). This computer runs software for periodic processing of the image of the prostate (4) and the needle (3) with respect to a reference image.

This reference image can be an invariable image of the prostate acquired at a time $t_0$, or a periodically refreshed image.

The computer determines information representing the movement of the prostate, involving:

a general displacement of the prostate in the image acquired at a time t, with respect to the reference image, a general rotation of the prostate in the image acquired at a time t, with respect to the reference image, a deformation of the prostate in the image acquired at a time t, with respect to the reference image.

On the basis of this information representing the movement, the computer recalculates the insertion parameters and modifies the command to move the robot (10).

The objective of these computations is to make it possible to compensate for deformations mechanically induced by the stresses exerted by the needle, and indirectly by the rectal probe, on the prostate, which is a soft organ.

The computer makes it possible to apply the following computations:

1) calibration of the relative position of the needle and the rectal probe, 2) insertion of the rectal probe and positioning in order to ensure the acquisition of a prostate image, 3) acquisition of a three-dimensional reference image $I_0$ before the first insertion of the needle, 4) recording of the plan, 5) first displacement of the needle according to the first step of the plan, 6) acquisition of a new three-dimensional image $I_n$ corresponding to the new position of the needle, 7) calculation of the spatial transformation between the image $I_n$ and the initial image $I_0$ or the preceding image $I_{n-1}$, 8) determination in the image $I_n$ of the position of the head of the needle with respect to the target recorded in the plan, 9a) if the distance between the head of the needle and said target is below a threshold value, the needle is removed and a new insertion cycle is carried out starting with step 5 above, 9b) if the distance between the head of the needle and said target is greater than said threshold value, it is determined whether the target can be reached by an additional displacement of the needle, 9b1) if so, an additional displacement of the needle is performed according to an updated plan, and the cycle is taken up again starting with step 8 above, 9b2) if not, the needle is removed and the plan is recalculated in order to take into account the movement of the prostate, and the cycle is taken up again starting with step 5 above, for the target that has not been reached.

Figure 3:
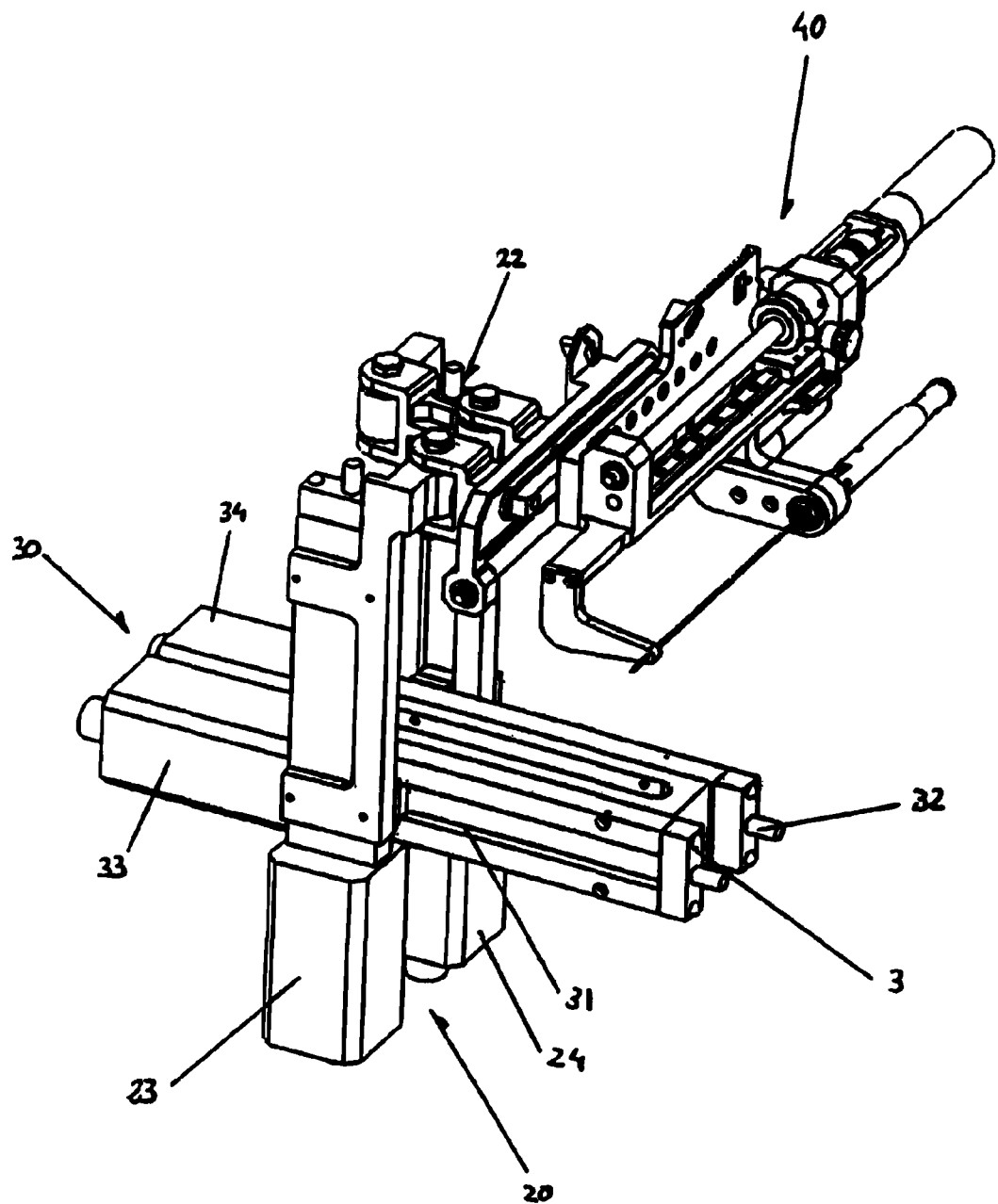
FIG. 3 shows an example of an embodiment of a needle-holding robot.

FIG. 3 shows an example of an embodiment of a needle holder robot.

It consists of a positioning module formed by two perpendicular frames (20, 30) consisting of deformable parallelograms. The mechanism ensuring the longitudinal displacement of the needle consists of an arm (40) pivotably connected to the first frame (20). The translational displacement axes of the two frames (20, 30) and the arm (40) are perpendicular and form a three-dimensional reference system.

The first frame (20) includes two parallel rails (21, 22) and two motors (23, 24). The arm (40) is pivotably connected to each of said rails (21, 22) by pivots enabling the needle holder (40) to be tilted in a plane parallel to the plane passing through the two median axes of the rails (21, 22).

This plane can itself be angularly oriented by an action of the second frame (30). This second frame (30) also includes two rails (31, 32) and two motors (33, 34).

Each rail (31, 32) is pivotably connected by a pivot to one of the rails (21, 22), respectively, of the first frame (20). By modifying the relative extension of one of the rails (31) with respect to the other parallel rail (32,) a rotation of the plane of the first frame about an axis perpendicular to a plane passing through the rails (31, 32) of the second frame (30) is caused.

Figure 4:
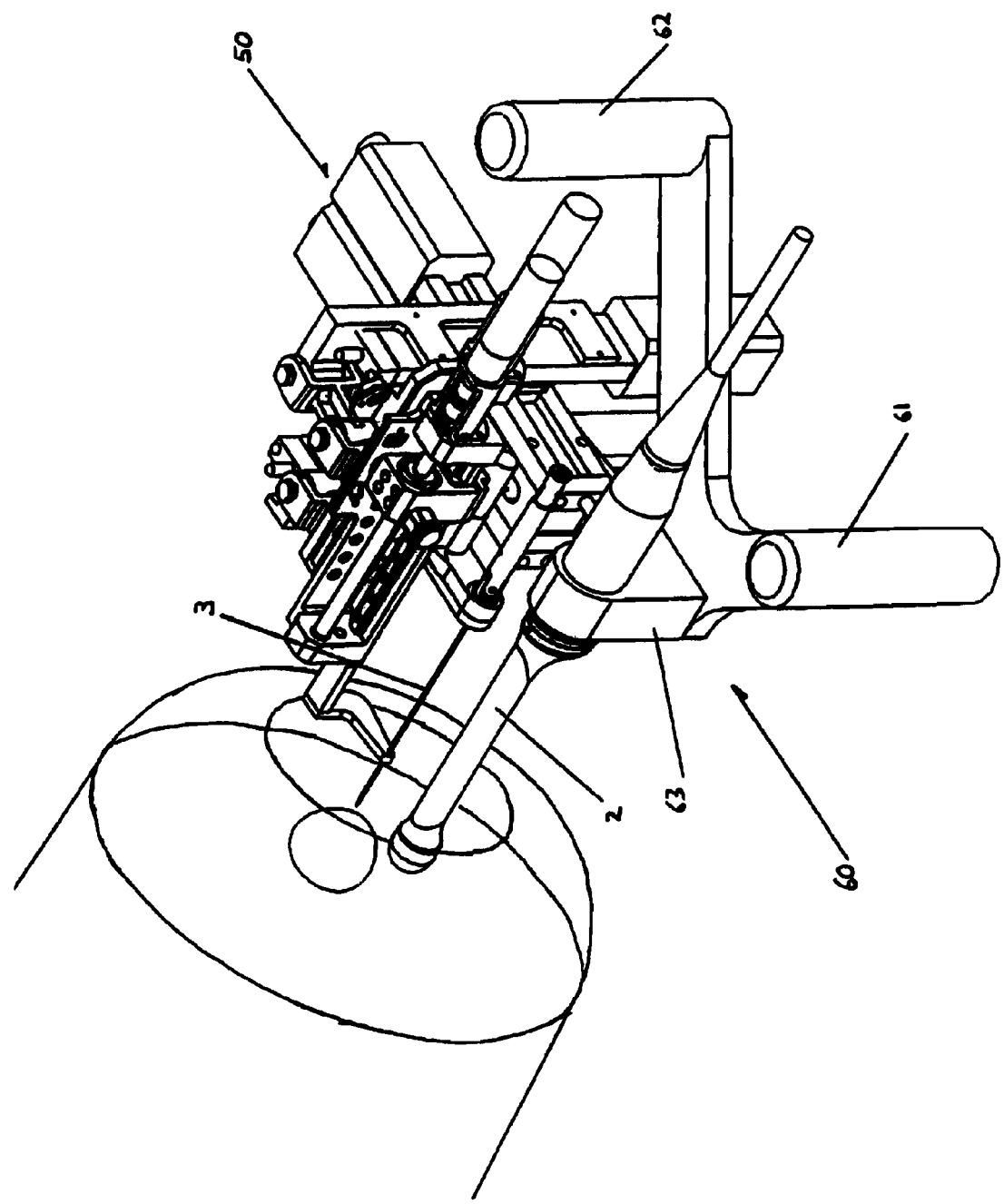
FIG. 4 shows an overview of the needle-holding robot.

FIG. 4 shows an overview of the needle holder robot.

The positioning module (50) is mounted on a support (60) having two arms (61, 62) intended for the handling of the robot by the surgeon. This support also includes an extension (63) for attachment of the rectal probe (2). The extension can optionally be pivotably connected so as to enable a modification of the angle formed between the axis of the rectal probe (2) and a reference axis of the positioning module (50).

Figure 5:
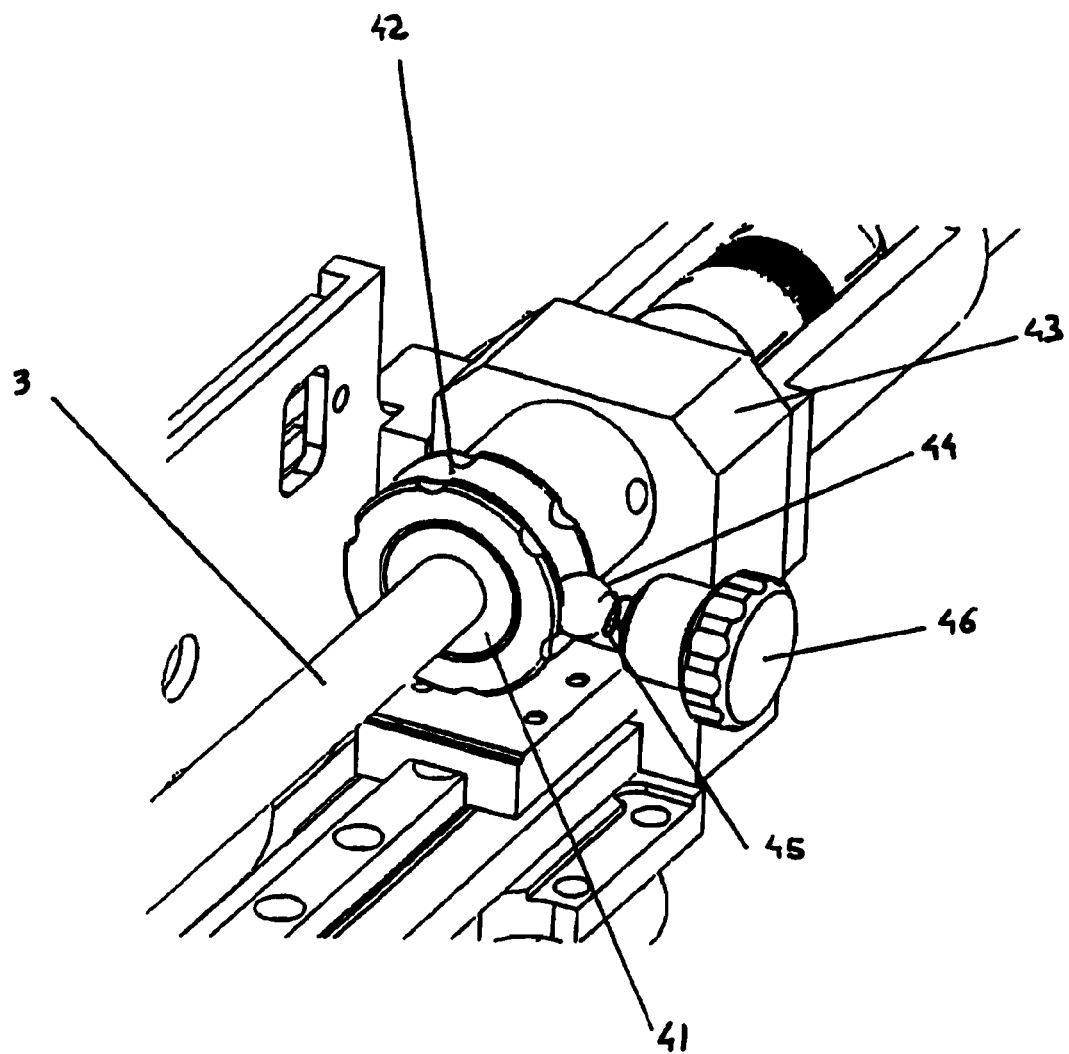
FIG. 5 shows a detailed view of the needle holder.

FIG. 5 shows a detailed view of the needle holder.

The needle (3) is interdependent with a cylindrical mandrel (41), having a groove (42). This mandrel (41) is engaged in a cylindrical cavity of a mobile head (43), which is partially shown, and the front portion is transparent in the drawing so as to enable the mandrel to be seen.

The cross-section of the cavity is substantially equal to the external cross-section of the mandrel (41), in order to enable an effortless longitudinal displacement between the mandrel (41) and the mobile head (43). The coupling between these two portions is ensured by a ball mechanism (44) including a spring (45) pushing the ball (44) into the cavity (42). An adjustment button (46) enables the calibration of the spring (45) to be adjusted.

This mechanism ensures the driving of the mandrel by the mobile head (43), with a limitation of the stress.

When the resistance encountered by the needle exceeds a threshold value, the ball (44) is pushed outside of the groove (42) and the mandrel is then disconnected from the mobile head (43).

The threshold value is determined on the basis of the resistance encountered by the needle when it stops inadvertently on the pubic bone.

Figure 6:
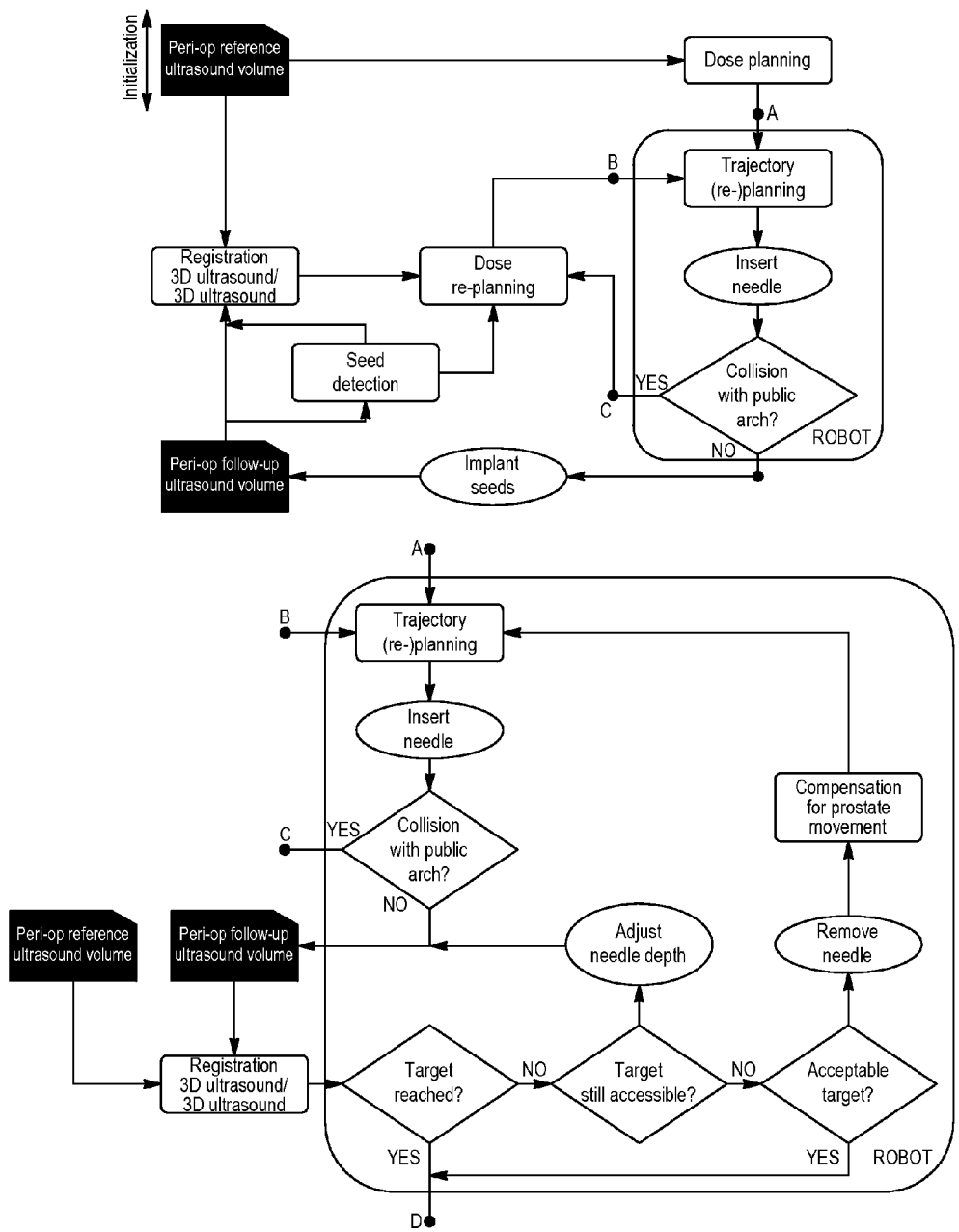
FIG. 6 shows a diagram of use of a preferred embodiment of the invention.

FIG. 6 shows a diagram of clinical use of a preferred embodiment of the invention.

At the beginning of the procedure, a 3D ultrasound volume is acquired, in which the contour of the prostate and the initial dose plan are determined. In this initial planning phase, the needle trajectories and the seed positions are defined with respect to the reference prostate extracted from the reference ultrasound volume. Then, the following process is applied for each needle: the needle trajectory calculated in the coordinate reference system of the robot in a preliminary step of calibration of the ultrasound probe with respect to the robot. The robot positions the needle at its insertion point at the level of the perineum, and inserts it. If the pubic arch interferes, the needle is removed and a partial plan is again calculated in order to modify the trajectory of the needle while preserving the dose constraints. Once the needle is inserted at the planned position, a verification procedure is applied in order to check for and overcome any displacement or deformation of the prostate caused by the insertion of the needle. Once the clinician has obtained the final position of the needle, the seeds are inserted while the needle is progressively removed. A 3D ultrasound volume can be acquired at this time in order to verify the position of the seeds of said needle, generally or individually: an image processing makes it possible to precisely locate the prostate and the seeds, after which a new plan may be necessary in order to take into account remaining imprecisions, in the final positioning of the seeds, for example. During the re-planning steps, biomechanical models may advantageously be used in order to better predict the movements of the organs. It is important to note that, in the monitoring schema presented, the reference system of the dosimetry plan is associated with the mobile prostate, rather than with the stationary ultrasound probe, as is the case in the conventional procedure. The acquisition of a second ultrasound volume and the updating thereof with respect to the reference volume makes it possible to deform the dosimetry plan according to prostate movements, and thus to verify that the needle is located in the expected position in the prostate. Otherwise, the user or the system verifies whether the deformed target is still accessible via the same needle trajectory, in which case the needle depth is adjusted. Alternatively, if the clinician considers the current position of the needle to be unacceptable, it is removed and a partial plan is again calculated in order to compensate for the prostate movements before the needle is inserted.

The invention claimed is:

1. A needle holder device for a prostate treatment involving a sequence of steps of inserting a needle into the prostate, comprising a 3D rectal ultrasound volume imaging probe of the prostate and a computer configured to process an image acquired by said probe and to calculate a position of the needle with respect to the prostate, wherein the computer is commanded to periodically deliver information on movement of the prostate after each of said insertion steps in order to validate insertion parameters with respect to a treatment plan, and to modify the insertion parameters with respect to said plan in the event of a movement having a value greater than a threshold value, and the information relating to the three-dimensional movement of the prostate is calculated by comparison of an instantaneous image delivered by the rectal probe with a reference three-dimensional image of the prostate and by the calculation of quantitative information on modifications between said instantaneous and reference images, wherein the computer determines information representing the movement of the prostate, involving: a general displacement of the prostate in the three-dimensional image acquired at a time t, with respect to the reference three-dimensional image, a general rotation of the prostate in the three-dimensional image acquired at the time t, with respect to the reference three-dimensional image, and a deformation of the prostate in the three-dimensional image acquired at the time t, with respect to the reference three-dimensional image.

2. Device according to claim 1, wherein said modification of insertion parameters consists of modifying the plan.

3. Device according to claim 1, wherein said modification of insertion parameters consists of modifying the insertion parameters by a new displacement of the needle.

4. Device according to claim 1, wherein the computer is capable of calculating a distance between a characteristic point of the needle in an instantaneous prostate reference system and said characteristic point of the needle in a prostate reference system in the plan, and then of comparing said distance with said threshold value in order to conditionally validate the insertion parameter.

5. Device according to claim 1, further comprising a support extended by a rectal probe and a needle holder; and means for determining a relative orientation of the needle holder with respect to an acquisition volume of said rectal probe.

6. Device according to claim 5, wherein said needle holder is powered and controlled with respect to movement information, and comprises means for generating a signal representing each new insertion step.

7. Device according to claim 6, wherein said needle holder can be oriented so as to modify an insertion axis according to said plan.

8. Device according to claim 1, further comprising a support integrated with the rectal probe, associated with a pivotably connected needle holder assembly, consisting of two primary parallel drive tables, each said primary parallel drive table being connected to a secondary perpendicular drive table, in which the needle holder being supported by a cross member rotatably connected with respect to said secondary drive tables, in which said cross member extends perpendicularly to an axis of displacement of said secondary tables and an axis of displacement of said primary tables.

9. Device according to claim 8, wherein the needle holder comprises stress-limiting means mechanically disengaging the driving of the needle support with respect to the needle holder when the resistance to insertion exceeds a threshold value corresponding to a situation of contact with the pubic bone.

10. Device according to claim 1, further comprising a support associated, on the one hand, with a rectal probe and, on the other hand, with means for positioning a needle holder.

11. The device according to claim 8, wherein the cross member is rotatably connected with respect to said secondary drive tables by respective pivots, and pivots in a central plane parallel to the plane passing through the axes of the secondary tables, the primary table being each connected to one of the secondary tables so as to angularly orient the central plane.

12. The device according to claim 9, wherein the needle is interdependent with a cylindrical mandrel having a groove, the mandrel being engaged in a cylindrical cavity of a mobile head, a cross-section of the cylindrical cavity being substantially equal to an external cross-section of the mandrel, a coupling between the mandrel and the mobile head being ensured by a ball mechanism that comprises a spring capable of pushing a ball into the cylindrical cavity.

* * * * *